(12) United States Patent
Shadduck

(10) Patent No.: US 6,503,251 B1
(45) Date of Patent: Jan. 7, 2003

(54) OFFSET HELIX SURGICAL FIXATION SCREWS AND METHODS OF USE

(76) Inventor: John H. Shadduck, 1490 Vistazo West, Tiburon, CA (US) 94920

( * ) Notice: Subject to any disclaimer, the term of this patent is extended or adjusted under 35 U.S.C. 154(b) by 172 days.

(21) Appl. No.: 09/694,417

(22) Filed: Oct. 23, 2000

(51) Int. Cl.$^7$ ............................................. A61B 17/56
(52) U.S. Cl. ........................ 606/72; 606/73; 606/232; 606/60
(58) Field of Search ........................ 606/72, 73, 232, 606/60, 62, 64, 65, 67; 411/187, 389, 397, 395, 413, 411, 415, 385

(56) References Cited

U.S. PATENT DOCUMENTS

| | | | | |
|---|---|---|---|---|
| 5,234,430 A | * | 8/1993 | Huebner | 606/60 |
| 5,951,560 A | * | 9/1999 | Simon et al. | 411/414 |
| 5,964,783 A | * | 10/1999 | Grafton et al. | 606/232 |
| 6,027,523 A | * | 2/2000 | Schmieding | 606/232 |
| 6,045,573 A | * | 4/2000 | Wenstrom et al. | 606/232 |
| 6,099,529 A | * | 8/2000 | Gertzman et al. | 606/72 |

* cited by examiner

Primary Examiner—Pedro Philogene

(57) ABSTRACT

A surgical fixation screw that can be driven with significantly reduced torque thus allowing for theaded fixation bodies to be made substantially of bioabsorbable materials. The novel fixation body, also called an offset helix fixation body, extends along a first (central) axis. The fixation body comprises first and second helically-mating members that mate along a constant-lead helical interface that extends about a second (non-central) axis. The second axis is angularly offset from the first axis of the fixation body from about 1° to 20°. Alternatively, the second axis is parallel to, but laterally offset from, the first axis. Thus, the first and second members of the fixation body can travel helically relative to one another about the helical mating interface between a first insertion configuration and a second anchor configuration. In the insertion configuration, the screw's outer periphery has a first (lesser) transverse sectional dimension to allow reduced torque in helically driving the screw into a space in a bone. After being driven into a space or bore, the first and second members then can be moved helically relative to one another about the helical mating interface to an anchor configuration in which the screws outer periphery is expanded radially outward to provide a second (greater) transverse sectional dimension for securing the fixation body in the space or bore.

25 Claims, 9 Drawing Sheets

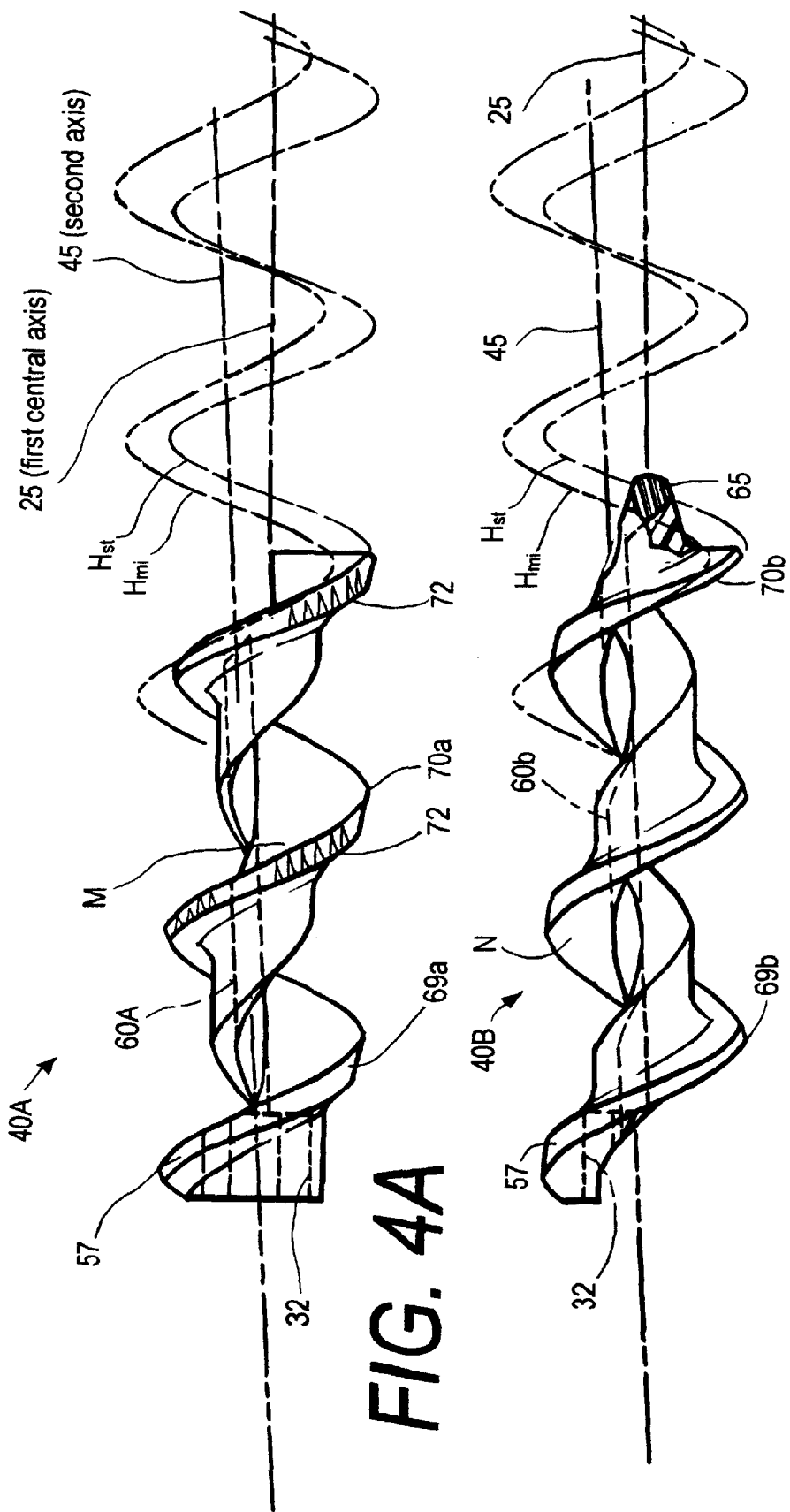

OFFSET HELIX SURGICAL FIXATION SCREWS AND METHODS OF USE

BACKGROUND OF THE INVENTION

1. Field of the Invention

This invention relates to surgical devices for fixing tissue, grafts and sutures to a patient's bone, and more particularly to biocompatible and bioabsorbable implantable screw-type devices capable of insertion into a bone with reduced torque on the implant and reduced stress on the bone.

2. Description of Prior Art

Many surgical procedures require attachment of tissue, grafts or sutures to a bone or other dense tissue surrounding a bone. For example, various forms of threaded screws have been disclosed for securing a suture in a bore in a bone (see, e.g., U.S. Pat. Nos. 5,209,753, 4,632,100). As another example, interference-fit type screws have been developed for driving into an endosteal bore to secure a bone graft such as in practiced in anterior cruciate ligament reconstruction (ACL) procedure. Such interference-fit screws and ACL methods are disclosed, for example, in U.S. Pat. Nos. 5,139,499, 5,139,520 and 5,234,430.

In the placement of anchor screws or interference-fit screws into a bore, the surgeon typically must apply a high level of torque to drive the screw inwardly to provide a secure attachment. If the endosteal bore is over-sized, any screw-type fixation device will be susceptible to loosening and failure. In driving an interference-fit screw in ACL reconstruction, a high level of torque typically is required which can cause an interference-fit screw to self-tap in an incorrect direction or to diverge from the axis of the endosteal bore. Insertion of such an interference-fit screw also may compress a graft undesirably or cause the bone graft to migrate in the bore, all of which are undesirable.

For both anchor screws and interference-fit screws, surgeons preferably would utilize a bioabsorbable implant fixation body. However, both anchor and interference-fit screws of a bioabsorbable material would be susceptible to shear failure or chipping of the threads during insertion into an endosteal bore, due to the lower strength of bioabsorbable material as compared to a metal alloy screw. There is, therefore, a need for improved anchor screws and interference-fit screws that can be driven with significantly less force, and particularly for such fixation devices that can fabricated of bioabsorbable materials.

SUMMARY OF THE INVENTION

The present invention comprises a two-component helically-threaded implantable fixation device for anchoring a graft, suture or tissue in a bore formed in a bone mass (endosteal bore, hereafter) that is actuatable between a first insertion configuration an second anchor configuration. The novel fixation body disclosed herein can be made of a biocompatible metal alloy, or partly or entirely of a bioabsorbable material.

The fixation device of the present invention utilizes a threaded fixation body, hereafter also called an offset helix fixation body, that extends along a first central longitudinal axis. The fixation body is formed of first and second helically-mating members. The fixation body typically defines at least one helical thread about an exterior of the body. The first and second members of the fixation body mate along a constant-lead helical interface, with such a helical interface defined by a radial extending from a second axis that is offset from the above-described first axis of the fixation body. By the term offset, it is meant that the second axis of the helical mating interface is angled from 1° to 20° or more from the first axis of the body. Alternatively, the second axis is parallel to, but laterally offset from, the first body axis. In this regard, the first and second members of the fixation body can travel helically relative to one another along the helical mating interface between a first insertion configuration and a second anchor configuration. In the insertion configuration, the screw's outer periphery has a first (lesser) transverse sectional dimension to allow reduced torque in helically driving the screw into an endosteal bore. After the screw body is driven into the endosteal bore, the first and second members are moved helically relative to one another a slight amount about the helical mating interface to the anchor configuration in which the screw's outer periphery is expanded radially outward providing a second (greater) transverse sectional dimension to thereby secure the fixation device in the bore. Such a screw can be driven into a bore with substantially reduced forces due to the lesser-dimensioned insertion periphery of the body. The final anchoring of the fixation device in the bore also is accomplished with reduced overall torque because only slight relative helical travel of the first and second members is required to move the body from the insertion configuration to the anchor configuration. Of particular interest, since offset helix screws use reduced torque for driving and are actuatable to anchor configuration, such screws can be made of bioabsorbable materials having less tensile strength than conventional metal alloy screws.

In general, the present invention advantageously provides surgical fixation screws and methods for anchoring tissue, grafts and other materials in an endosteal bore in a bone that requires reduced torque for driving into a bore.

The present invention advantageously provides a surgical fixation body made of first and second mating members that mate along a helical interface having an axis that is offset from an axis of the fixation body to provide an insertion periphery and an anchor periphery that have lesser and greater transverse sectional dimensions, respectively.

The present invention provides a fixation body having a first lesser-dimensioned insertion periphery for ease of driving into an endosteal bore and a second greater-dimensioned periphery for anchoring the screw in the bore.

The present invention provides a fixation body having an anchoring periphery that has an increasing transverse dimension in the distal direction for securing the screw body in a bore.

The present invention advantageously provides a fixation screw that requires reduced torque for initial insertion into an endosteal bore because only relatively shallow threads are cut in wall around the endosteal bore.

The present invention provides a bone screw that requires less torque in the final anchoring phase because only slight relative helical travel of the first and second members is required to move the members from the insertion configuration to anchor configuration.

The present invention advantageously provides a fixation screw in which reduced driving torque during insertion allows the screw threads to be formed of bioabsorbable material, and such threads will not tend to fracture or chip during the insertion phase.

The present invention advantageously provides a fixation screw made of helically mating bioabsorbable members (i) having a helical thread with flattened lands in an initial insertion configuration for driving into a bore, and (ii)

having a partially sharp edge in an anchoring configuration for cutting into the bone mass as the screw is anchored.

The present invention advantageously provides a fixation screw that can be cannulated for guiding over a guide rod.

The present invention advantageously provides an interference screw and method for a bone-tendon-bone graft in anterior cruciate ligament (ACL) reconstruction in which the interference-fit screw of the present invention will not cause the bone graft to migrate in the endosteal bore.

The present invention advantageously provides a fixation screw with a blunt nose for use in ACL reconstruction in which the screw will not self-tap or diverge from the axis of the endosteal bore.

Additional advantages and features of the present invention will be apparent in the following description, the accompanying drawings and the appended claims.

BRIEF DESCRIPTION OF THE DRAWINGS

FIG. 4A is an elevational view of the first member of the Type "A" fixation device assembly of FIGS. 1–2 de-mated from the second member.

FIG. 4B is an elevational view of the second member of the fixation device assembly of FIGS. 1–2 de-mated from the first member.

FIG. 5A being the fixation body with the first and second members in the first insertion configuration and positioned with its distal nose in a bore; FIG. 5B being the fixation body with the first and second members still in the first insertion configuration after being helically driven into the bore; FIG. 5C being the fixation body with first and second members moved toward the second anchor configuration to secure the body in the bore.

FIG. 10A being the fixation body with the first and second members in the first insertion configuration and positioned with its distal nose in a space between a wall of a bore and a bone plug that carries a graft; FIG. 10B being the fixation body still in the first insertion configuration after being helically driven into the space between the wall of the bore and the plug; FIG. 10C being the fixation body with the first and second members moved to the second anchor configuration to further compress the plug and graft against the wall of the bore.

DESCRIPTION OF PREFERRED EMBODIMENTS OF THE INVENTION

Figure 1:
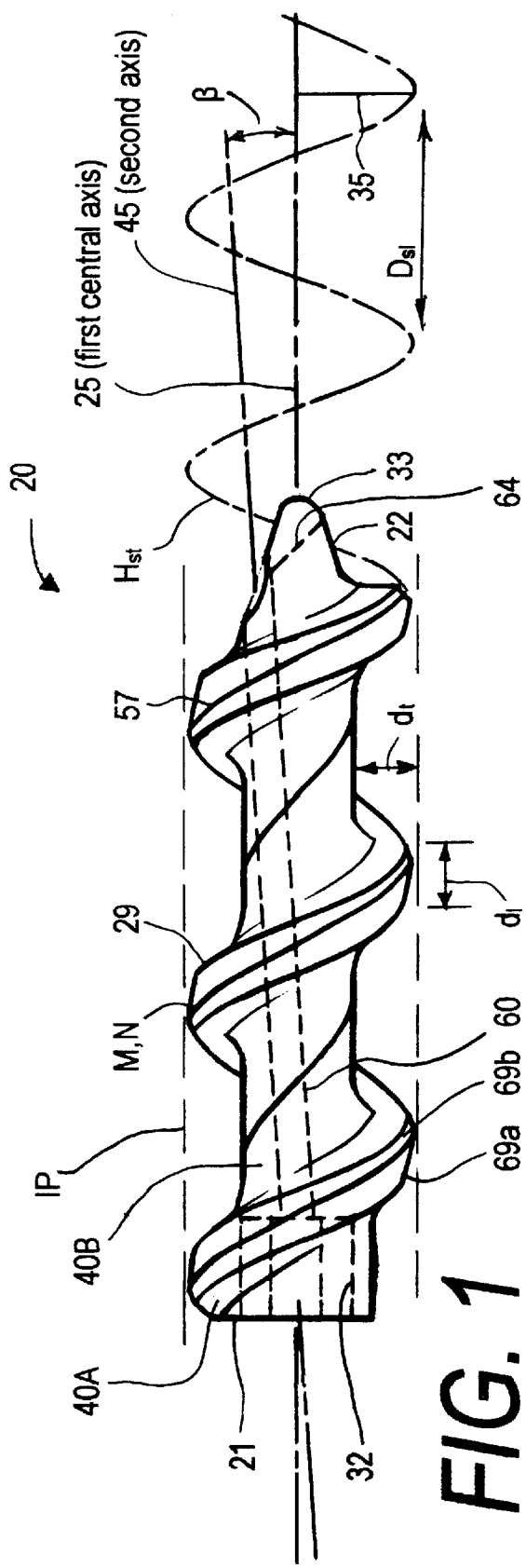
FIG. 1 is an elevational view of an exemplary Type "A" embodiment according to the invention that illustrates an offset helix fixation device with first and second members in a first insertion configuration.
Figure 2:
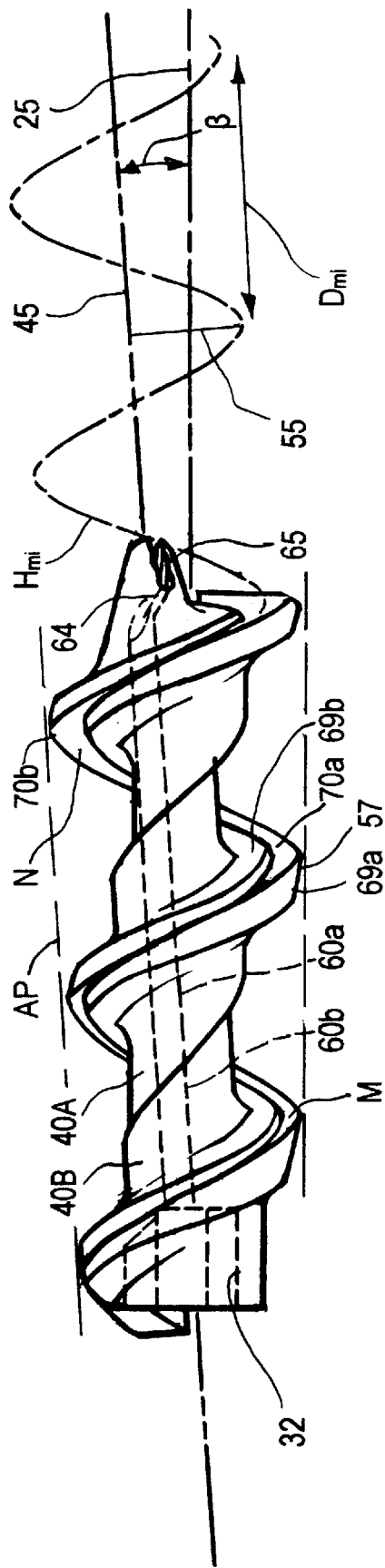
FIG. 2 is an elevational view of the Type "A" fixation device of FIG. 1 with the first and second members of the body assembly moved to a second anchor configuration.

1. Type "A" Offset Helix Fixation Body. By way of example, FIGS. 1 and 2 depict a Type "A" offset helix fixation body or screw body 20 adapted for securing a suture or elongate graft in a bone mass. Several dimensions and helix forms are applicable to all fixation bodies illustrated in the drawings and are indicated as follows:

IP: insertion periphery (i.e., outermost periphery of threaded body 20 in an insertion configuration)

AP: anchor periphery (i.e., outermost periphery of threaded body 20 in an anchor configuration)

Figure 3:
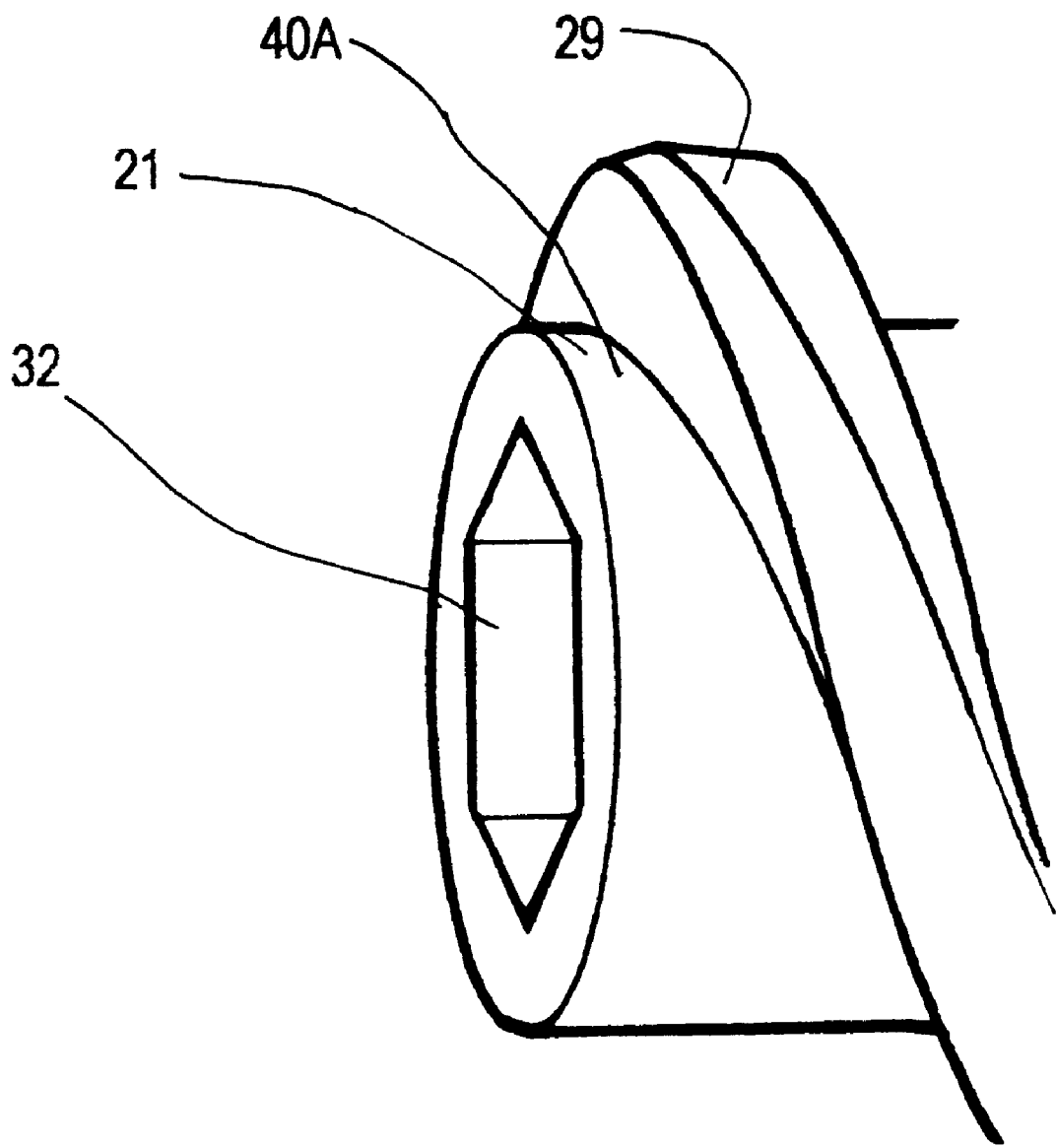
FIG. 3 is a view of the proximal end of the fixation body of FIG. 1 showing an axial-extending polygonal socket for receiving a driver.

$H_{mi}$: helix defining the mating interface $D_{mi}$: dimension of spiral lead defined by helical mating interface M and N: mating surfaces of first and second members, respectively $H_{sl}$: helix defining the spiral thread $D_{sl}$: dimension of spiral lead defined by thread dl: dimension across lands of threads dt: depth of threads Referring to FIG. 1, the fixation body 20 is illustrated in an insertion configuration (or first position) with an outer insertion periphery IP defined by the thread periphery that has a generally cylindrical shape about the length of the body assembly. The screw body assembly 20 has proximal end 21 and distal end 22 with the body extending about a first (central or longitudinal) axis 25. A helical thread 29 is shown in a single-lead although it should be appreciated that plural-lead threads fall within the scope of the present invention. As shown in FIG. 3, the proximal end of body 20 in the first position defines an axial-extending polygonal socket 32 for receiving a driving end of a conventional polygonal driver, for example a hexagonal driver. The distal end of body assembly 20 has a tapered nose portion indicated at 33.

Still referring to FIG. 1, the spiral thread 29 has a substantially constant spiral lead defined by a helix indicated at $H_{sl}$. The spiral lead of the thread has a dimension $D_{sl}$ that is represented in FIG. 1 as the axial travel resulting from an angular movement of 360° of line 35 extending orthogonal to axis 25 outwardly as the line passes through a helix around first axis 25. As such, the spiral lead dimension $D_{sl}$ generally is equal to the axial travel of the threaded body 20 in a bone mass through 360° rotation. Such spiral lead dimension $D_{sl}$ can range from about 1 mm. to about 50 mm. More preferably, the spiral lead dimension $D_{sl}$ ranges from about 2 mm. to about 10 mm.

Referring now to FIGS. 1 & 2, body 20 comprises an assembly of first member 40A and second member 40B that mate along helical mating interfaces or surfaces M and N that extend around a second axis indicated at 45 (see FIG. 2). As can be seen in FIG. 2, the body assembly 20 is capable of transforming to an anchor configuration (second position) in which an anchor periphery AP has an increasing transverse dimension in the distal direction. FIGS. 4A and 4B illustrate first and second members, 40A and 40B respectively, de-mated from one another. In FIGS. 4A and 4B, the helices $H_{st}$ and $H_{mi}$, and their respective axes 25 and 45, that define both the spiral lead of the threads 29 and mating interface are shown.

Referring again to FIGS. 1 & 2, the mating interfaces M and N are defined by a helix indicated at $H_{mi}$ that has the spiral lead dimension $D_{mi}$, of the mating interface. The helical surfaces M and N can be more particularly defined by a line indicated at 55 that extends orthogonal to axis 45 outwardly as the line passes through a helix around axis 45. As can be seen in FIGS. 1 & 2, the second axis 45 of the mating interface is angularly offset from the first axis 25 of the body by approximately 5° indicated β. In this embodiment, the first and second helical axes may angularly be offset from about 1° to about 20°. The dimension of the spiral lead defined by helical mating interface is indicated at $D_{mi}$ and such dimension ranges from about 1 mm. to about 100 mm., and more preferably ranges from about 2 mm. to about 20 mm. In the preferred embodiment shown in FIGS. 1 & 2, it should be noted that dimension of the lead of the mating interface cooperates with the dimension of lead of the spiral thread to thereby allow the mating interface to fall substantially within the lands 57 of the threads over the length of body assembly 20.

In FIGS. 1 & 2, it can be seen that a central bore portion 60a in first member 40A and bore portion 60b in second member 40B are aligned in the second anchoring position (FIG. 2). In the first insertion position of FIG. 1, the bore portions 60a and 60b are offset since the first and second members 40A and 40B are counter-rotated. In this preferred embodiment, the central bore 60 of body assembly 20 (defined by bore portions 60a and 60b) is adapted for carrying a suture or other similar type of anchor material or loop. As can be seen best in FIG. 2 and FIG. 4B, the distal portion of second member 40B carries an angled slot 64 with a cleat structure 65 for gripping a suture as described below in FIGS. 5A–5C. Alternatively, as will be described below, a suture may be directly connected to a proximal end of the fixation body 20 through a bore or by any suitable means.

The first and second members 40A or 40B of body 20 of FIGS. 1 & 2 may be made of any biocompatible implantable material, e.g., stainless steel, titanium or a polymer such as Delrin® polyacetal. As shown in the accompanying drawings, the fixation bodies generally are depicted with threads having flat or rounded lands 57 (in the first insertion configuration of FIG. 1) that are suited for bodies made of a bioabsorbable material having less tensile strength that a metal alloy. As shown in FIG. 1, the spiral thread 29 has a flattened crest or lands 57 that defines dimension dl across the lands that ranges from about 0.5 mm. to 5.0 mm. The depth of the thread is indicated at dl and may be any suitable dimension. If the threads of a bioabsorbable body were substantially sharp, the crests of the threads would likely chip or fracture during insertion. The flattened crest of spiral thread 29 allows fixation body 20, along with the ability to actuate the body to an anchor configuration, allows the body to be formed of bioabsorbable material. Bioabsorbable materials for a fixation body (or one element of a fixation body) include materials such as polylactic acid (lactide), polygloycolic acid (glycolide) as disclosed in U.S. Pat. No. 3,739,773 (Schmitt, et al.), or co-polymers disclosed in U.S. Pat. No. 4,340,565 (Rosensaft et al.) and U.S. Pat No. 4,429,080 (Casey, et al.), the disclosures of which are all incorporated herein by reference. Other bioabsorbable materials are known, such as dioxanone, caprolactone, trimethylene carbonate, and mixtures thereof Referring to FIGS. 4A–4B, it can be seen that the first and second members, 40A and 40B, each define a thread portion 69a and 69b that combine to provide the spiral thread 29. As can be seen in FIG. 1, body assembly 20 in the first insertion position has flattened threads that are dimensioned to allow it be helically driven into a cooperating size of bore. Then, as can be seen in FIG. 2, the body assembly 20 in the second anchoring position will provide substantially sharp edges indicated at 70a and 70b. Such thread edges 70a and 70b will be exposed as the first and second members 40A and 40B are moved toward the second in anchoring position thus allowing the body 20 to cut or bite into the bone as the body is anchored. As shown in FIG. 4A, the first member 40A optionally can have gripping teeth or serrations indicated at 72 to help prevent that member from backing out a path that the threads cut in a bone.

Figure 5A:
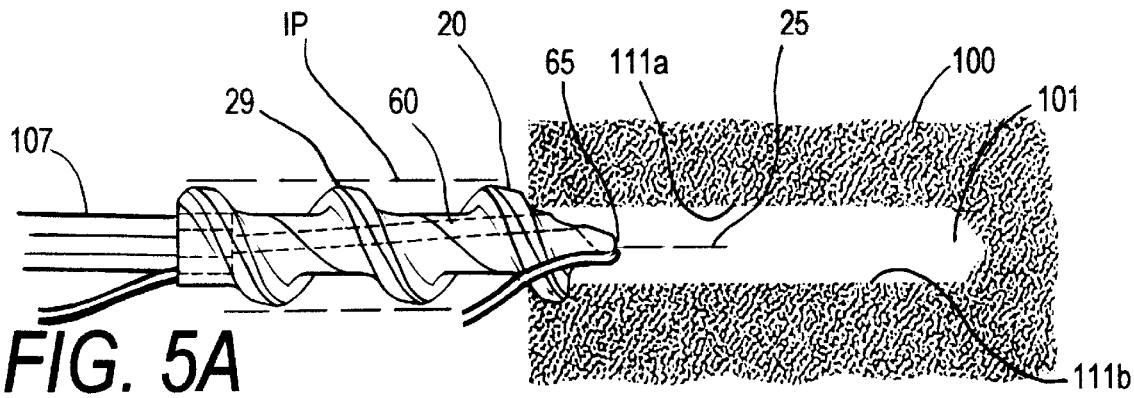
FIGS. 5A–5C are sectional views illustrating a method of the present invention in utilizing the Type "A" fixation device of FIGS. 1–2 as an anchor screw.
Figure 5B:
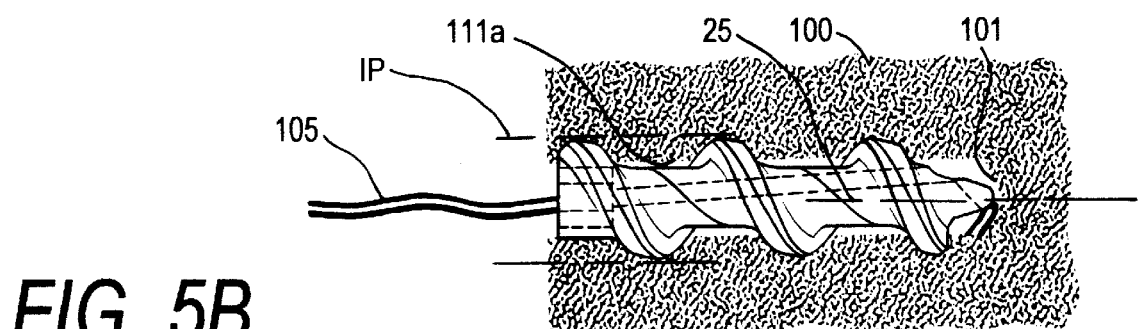
Figure 5C:
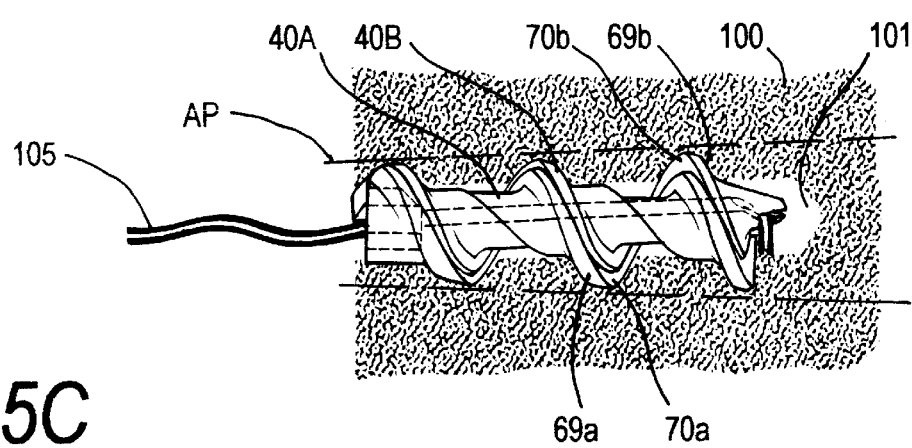

2. Method of Use of Type "A" Offset Helix. Turning now to FIGS. 5A–5C, bone mass 100 has endosteal bore 101 drilled therein that has a suitable diameter to receive the fixation body. The Type "A" fixation body 20 is illustrated in the steps of securing a suture 105 in bore 101. In FIG. 5A, the suture 105 is threaded through bore 60 and gripped in cleat 65 in the distal nose 33 of the screw body. The body 20 is moved to the first insertion position in which the outer insertion periphery IP defined by the crest of the threads 29 is substantially cylindrical. FIG. 5A shows the distal tip 107 of a hexagonal driver that is pushed into socket 32. Suture 105 may be squeezed to allow the driver tip to fit snugly in socket 32 or the socket or the tip 107 of the hexagonal driver may have a notch to accommodate the suture. FIG. 5B shows that body assembly 20 after being helically driven into bore 101 with the threads 29 biting a predetermined amount into the wall portions 111a and 111b around bore 101. By designing the cooperating dimensions of the bore and the screw's outer insertion periphery IP, the fixation body can be driven with reduced torque when compared to a prior art bone screw that would be dimensioned to bite deeply into the wall of the bore. Bore 101 is not a pilot bore to guide body 20, but is dimensioned so that the spiral thread 29 engages the walls of bore 101 to a depth substantially less than the depth of the thread indicated at dl (see FIG. 1).

FIG. 5C shows the fixation body after being driven a desired depth within bore 101. The physician then can pull proximally on suture 105 which will cause the second member 40B to counter-rotate relative to first member 40A toward the second anchor configuration in which the body's anchor periphery AP has an increased transverse dimension in the distal direction. Thus, greater proximal tensioning forces on suture 105 will cause the screw body 20, and more particularly the sharp edges 70b of thread portion 69b to cut more deeply into walls 111a and 111b around endosteal bore 101. Thus, both exposed sharp edges 70a and 70b of the thread portions 69a and 69b will be pushed radially (helically) outward to bite into the walls 111a and 111b in the drawings at the same time as increasing the cross-section of the distal portion of the device.

In another manner of anchoring the fixation body, it should be appreciated that a rotational force can be applied to either the first member 40A or second member 40B while the other member is maintained in a fixed configuration to move body assembly 20 to the second anchor position of FIG. 5C to thereby expand the distal cross-section of the body provide the anchor periphery AP. It also should be appreciated that a suture or a tissue may be attached to such a Type "A" fixation body in various ways, e.g., a suture or loop may be fixed to the proximal end of either the first or second member, 40A or 40B, or a suture may extend through a bore in a sidewall of the proximal end of the body and be knotted in various manners to be secured to the body 20.

3. Method of Making Offset Helix Body. The offset helix fixation body of FIG. 1, and more particularly each of the first and second members 40A and 40B, can be fabricated by injection-molding or casting of bioabsorbable components, or EDM methods (electrical discharge machining) or other machining methods for metal components. For the purposes of this disclosure, the following describes a method of the invention for fabricating the component parts of an offset helix from a threaded blank. It should be noted that the exemplary method utilizes wire-electrode EDM machining and is suitable for manufacturing the mating elements of the fixation device from a metal alloy. Alternatively, the EDM method disclosed next may be utilized in fabricating tooling (i.e., a mold or castings) for manufacturing mating elements of the offset helix of an injection-moldable or castable material. Assume that spirally-threaded body having the exterior shape of FIG. 1 is provided as a blank that comprises a single piece body. Such a helically threaded blank can be made in the indicated shape by a conventional helical tool and cutter grinder, by a Swiss screw machine or by other conventional machining methods. The blank is of any suitable metal, for example, medical grade stainless steel or titanium for an implant. The helically threaded blank thus defines a single-start constant spiral lead thread 29 with a spiral lead dimension $D_{sl}$. The blank can be machined into the first and second members illustrated in FIGS. 4A–4B with a multi-axis wire EDM machine that has a fully synchronized rotational axis or "C". The blank is mounted in the "C" axis drive such that axis 25 of the blank (see FIG. 1) is offset and desired amount, e.g., about 5°, from the centerline of the "C" axis about which the blank will rotate. The EDM wire is the held on an axis, e.g, the "Y" axis, at 90° relative to the "C" axis. The "Y" and "C" axes are then programmed to move in a synchronized manner both axially and angularly (i.e., helically) to cut a constant spiral lead through the blank through a selected path that is substantially aligned with the lands 57 of thread 29. The EDM wire will cut a path that defines the interface of the M and N surfaces as shown in FIG. 4. The component parts may be de-mated by helically separating one from the other. It should be appreciated that tolerances between mating parts may be reduced by cutting the first and second members from separate blanks and adjusting the parameters of the "Y" axis' movement, to provide for example tolerances as little as about 0.001". Further, the above method is best adapted for fabricating mating parts with a double-lead thread, but it will be obvious how the method can be used to fabricate the mating parts of a single-lead body. It can be easily understood that a similar method may be used to fabricate the component parts with a sinker-type EDM machine with a rigid electrode instead of a wire electrode.

Figures 6, 7:
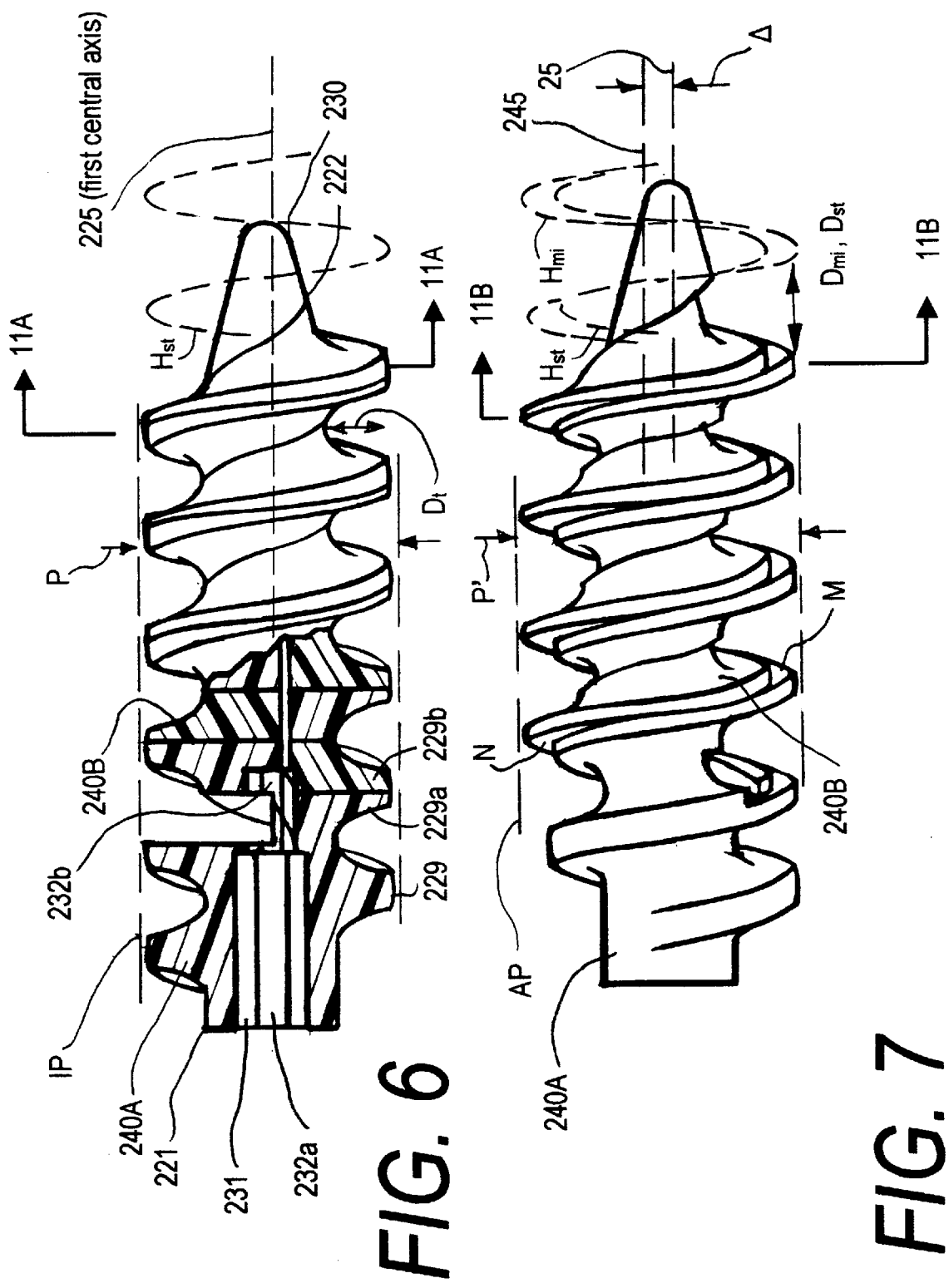
FIG. 6 is a cut-away elevational view of an exemplary Type "B" offset helix fixation device for functioning as an interference-fit screw, the body having the first and second members in a first insertion configuration.
FIG. 7 is an elevational view of the Type "B" fixation device of FIG. 6 with the first and second members in the second anchoring configuration.
Figure 10A:
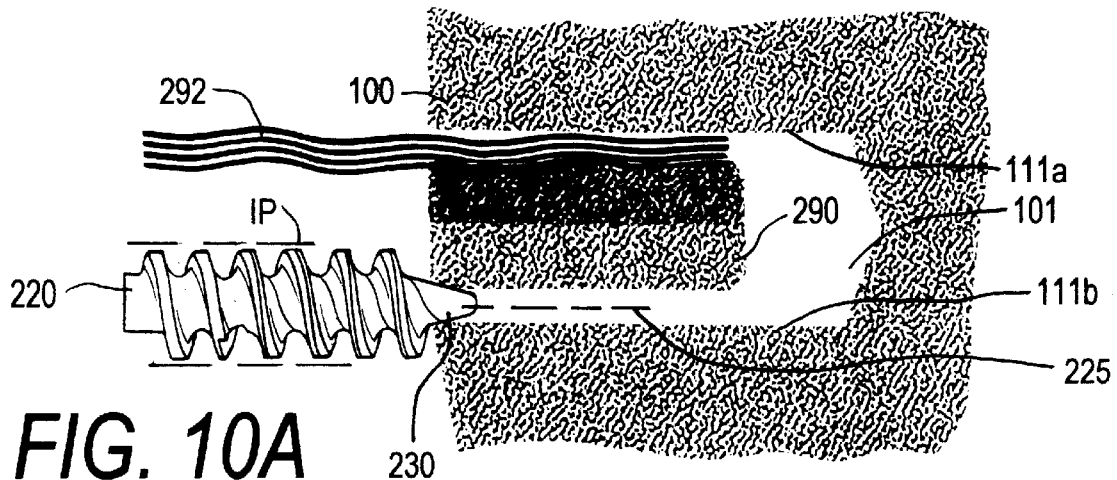
FIGS. 10A–10C are sectional views illustrating a method of the present invention in utilizing the Type "B" fixation device of FIGS. 6–7 as an interference-fit type screw to fix a graft in an bore.
Figure 10B:
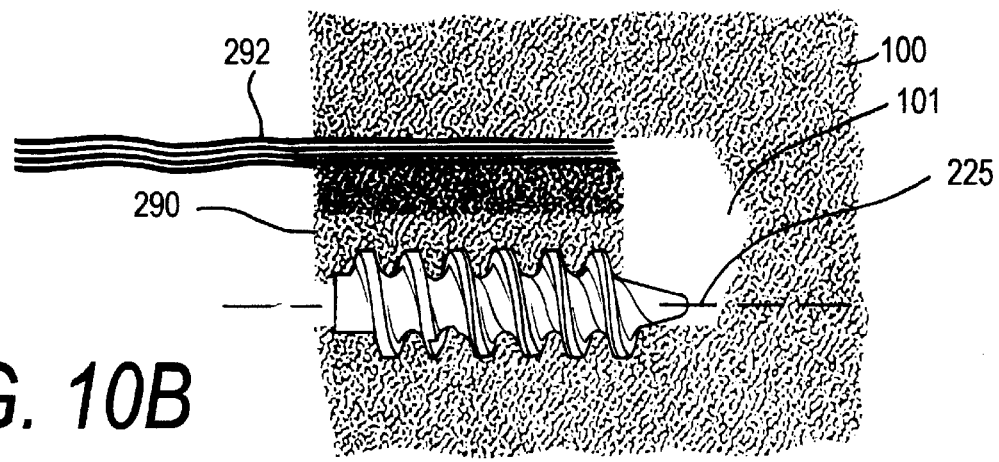
Figure 10C:
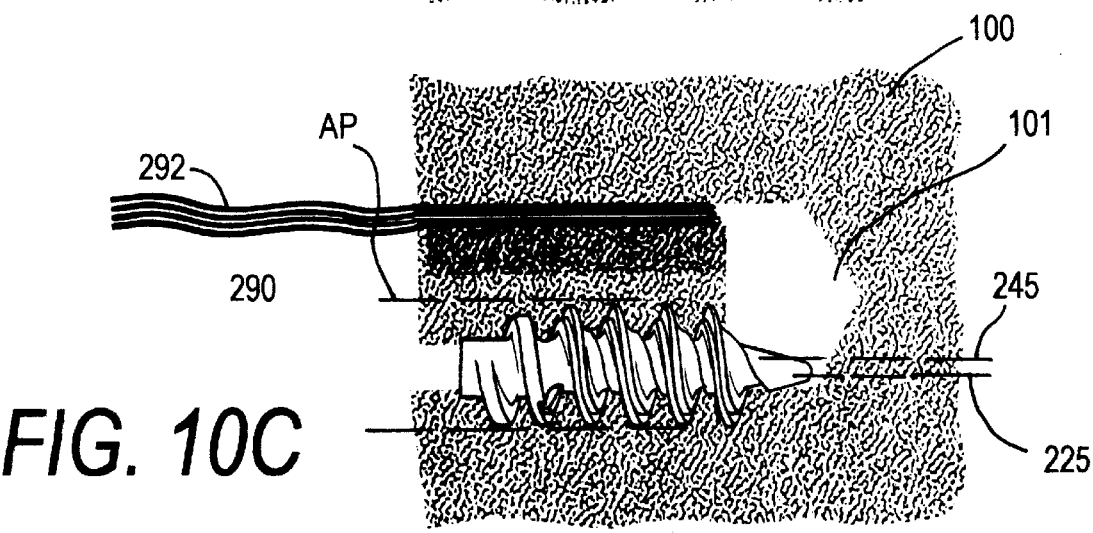

4. Type "B" Offset Helix Fixation Body. FIGS. 6–7 depict a Type "B" offset helix body 220 that comprises an interference-fit screw and is illustrated in FIGS. 10A–10C in securing a graft in a bore, for example as in an anterior cruciate ligament (ACL) reconstruction. The Type "B" screw body of FIGS. 6 & 7, illustrates (i) that an offset helix body can have a (second) mating helix axis 245 that is parallel to, but offset from, the (first) central body axis 225 to provide insertion and anchor configurations, (ii) that an offset helix body can be provided with grip elements about the mating interfaces M and N of resilient first and second members for locking the first and second members in the anchor configuration, and (iii) that an offset helix body can be provided with a first or second member that is driven distally relative the other member to move the body to the anchor configuration from the insertion configuration.

Referring to FIG. 6, body assembly 220 is illustrated in a first insertion position or configuration with the screw's outer insertion periphery IP having a generally cylindrical shape. Body 220 extends from proximal end 221 to distal end 222 about a first body axis indicated at 225. Spiral thread 229 is shown in a single-lead having a dimension $D_{sl}$. The body 220 has a tapered nose portion 230 and a proximal polygonal socket 231 for receiving a polygonal driver having from two to 10 or more faces.

As can be seen in FIG. 6, the body assembly 220 comprises a first member 240A and second member 240B that mate along an interface between the helical mating surfaces M and N of the respective members 240A and 240B. The mating surfaces M and N extend around a second axis 245. Now turning now to FIG. 7, it can be seen that body 220 is capable of transforming to a second anchor position in which the anchor periphery AP has a greater transverse or cross-sectional dimension than the insertion periphery IP of the body assembly 220 in the first position (see FIG. 6). In this embodiment, the mating surfaces M and N are defined by a helical mating interface $H_{mi}$ that has lead dimension $D_{mi}$ and extends around a second axis 245 that is laterally offset, but parallel to, the first body axis 225 by a range of about 0.5 mm. to 5 mm. indicated at Δ (see FIG. 7). As can be seen in the exemplary embodiment, the spiral lead dimension of the mating helical interface is similar to the dimension of the spiral lead of thread 229. As can be seen in FIGS. 6 and 7, the sectional dimension P of a transverse line across the periphery in the insertion configuration of FIG. 6 is increased to the dimension P' across the periphery in the anchor configuration of FIG. 7.

Figure 8A:
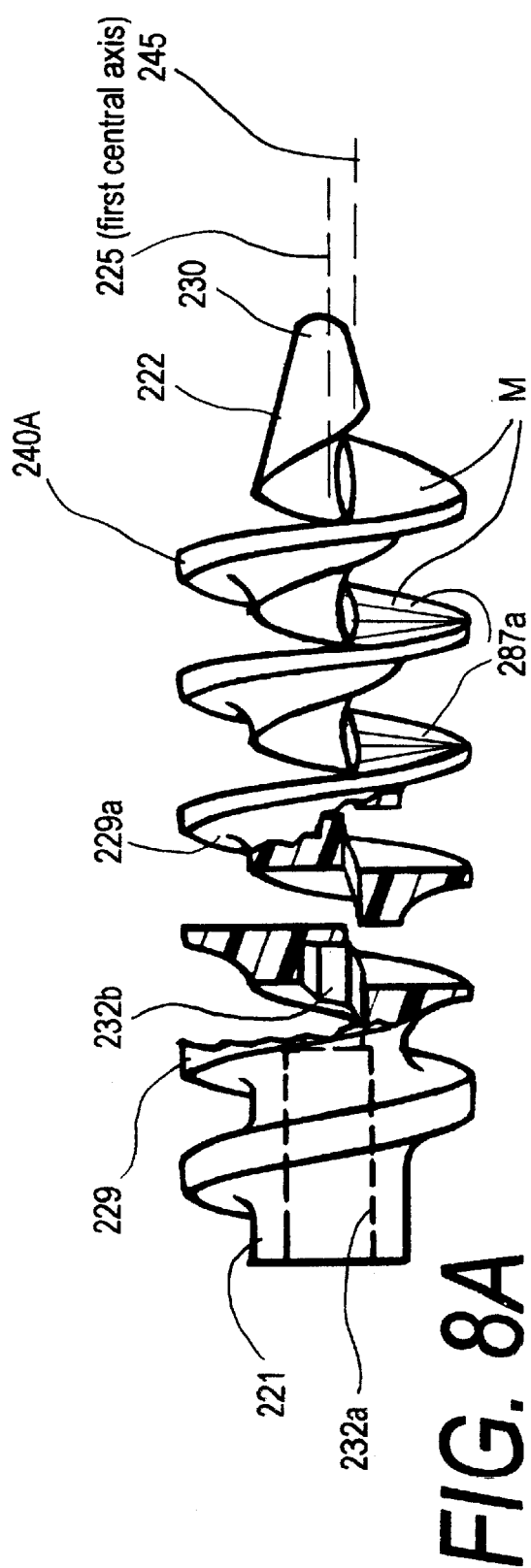
FIG. 8A is an elevational view of a first member of the Type "B" fixation device of FIG. 6 de-mated from the second member.
Figure 8B:
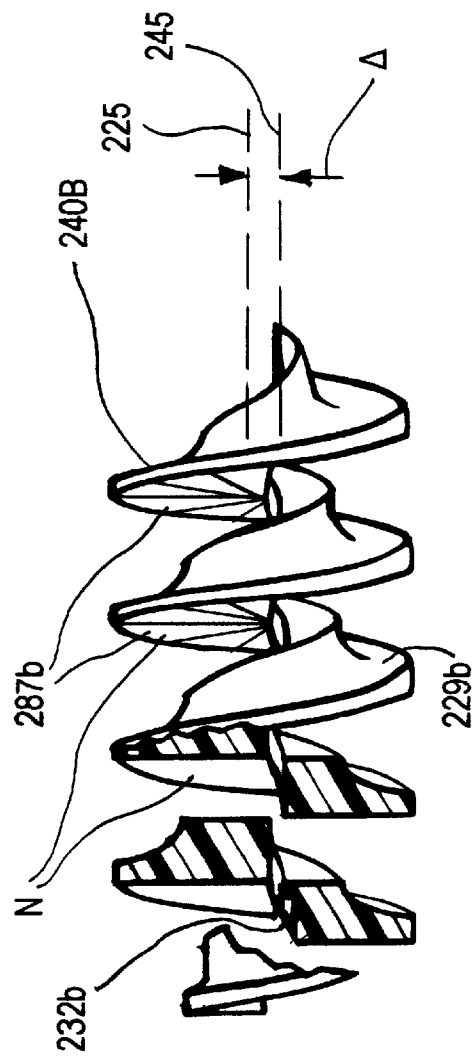
FIG. 8B is an elevational view of the second member of the fixation device of FIG. 6 de-mated from the first member.

Referring to FIGS. 8A–4B, the first and second members, 240A and 240B, of the body assembly are illustrated de-mated from one another. It can be seen that polygonal socket structure 231 is formed in the proximal end of the body assembly that further comprises a larger cross-section proximal socket portion 232a and a smaller cross-section distal socket portion 232b. FIG. 8A shows that proximal socket portion 232a is carried entirely within first member 240A. FIGS. 8A & 8B together illustrate that distal socket portion 232b extends through portions of both the first and second members 240A and 240B.

Figure 9A:
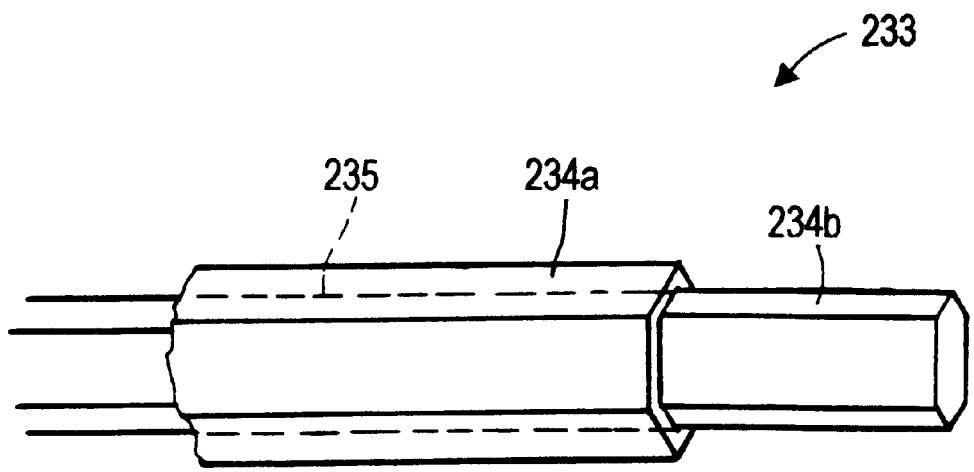
FIGS. 9A–9B are views of the distal end of a polygonal driver in first and second positions, respectively, for driving the Type "B" fixation device of FIGS. 6–7 in the insertion configuration and the anchor configuration.
Figure 9B:
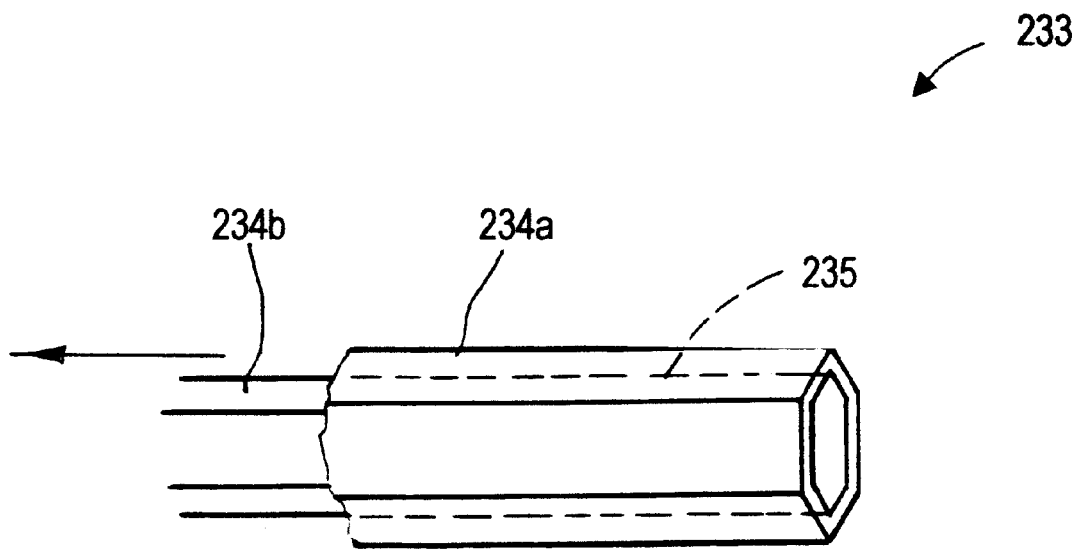

FIGS. 9A–9B show the distal end the polygonal driver 233 that is adapted to cooperate with fixation body 220. It can be seen that the driver 233 comprises concentric outer driver member 234a and inner driver member 234b that is slidable in polygonal bore 235 of the driver assembly. It can be easily understood that the driver in the configuration of FIG. 9A is adapted to engage polygonal socket portions 232a and 232b in the both the first and second members 240A and 240B as when driving the fixation body in a bore (see FIG. 6 and FIGS. 9A–9B). It can be seen that the driver in the configuration of FIG. 9B is adapted to engage only polygonal socket portion 232a in first member 240A for rotating or driving that member independent of second member 240B.

Referring to FIGS. 8A–8B, the first and second members 240A and 240B have helicoidal mating surfaces M and N that are exposed to view and are optionally impressed with radial serrations 287a and 287b. Thus, as the first and second members 240A and 240B are counter-rotated, serrations 287 (collectively) will engage one another and assist in locking the first and second members in any counter-rotated or anchor position. When the first and second members 240A and 240B are fabricated of a resilient bioabsorbable material with suitable tolerances, the surfaces M and N can deform slightly during counter-rotation of members 240A and 240B to thus allow the serrations 287 to ride over one another.

5. Method of Use of Type "B" Offset Helix Body. Turning now to FIGS. 10A–10C, the bone mass indicated at 100 has bore 101 formed therein. In the case of ACL reconstruction surgery, bore 101 is formed in either the distal femur or proximal tibia (or both) and bore 101 may have a closed end or extend through bone mass 100. For example, in a bone-tendon-bone graft. FIG. 10A depicts bone graft portion 290 including tendon 292 affixed thereto that is positioned in bore 101 in the distal femur. Bore 101 may be drilled with a conventional orthopedic drill employing endoscopic procedures. With graft 290 in the configuration depicted in FIG. 10A, the fixation body 220, and more particularly socket 231 thereof, is coupled with the distal end of the polygonal-tipped driver 233 in the configuration of FIG. 9A The surgeon inserts distal nose 230 of fixation screw 220 in the space between bone portion 290 and wall 111b of endosteal bore 101 as shown in FIG. 10A. Thereafter, the surgeon presses axially on fixation body 220 with the driver and contemporaneously commences rotation of the screw thereby causing thread 229 to engage bone graft 290 and wall 111b. The distal and helical advancement of fixation body 220 causes threads 229 to cut into bone graft 290 and wall 111b and gradually compresses bone graft 290 against the opposite wall portion 111a of bore 101. The diameter (i.e., insertion periphery IP) of the fixation body is selected to cooperate with the space between the bone plug and the waft of the bore. That is, the diameter of the screw is selected drive easily into the space with limited torque as the threads cut a shallow depth in the plug and the opposing wall. FIG. 10B shows body 220 after being helically driven, with reduced torque, into the space between bone graft 290 and the wall 111b of bore 101. The fixation body 220 for ACL reconstruction may be manufactured in various diameters in the insertion configuration, for example from 3 mm. to 10 mm. The diameter is selected so that thread 229 engages bone plug or graft 290 and walls of bore 101 to a depth less than the depth of thread dt (see FIG. 6).

Figure 11B:
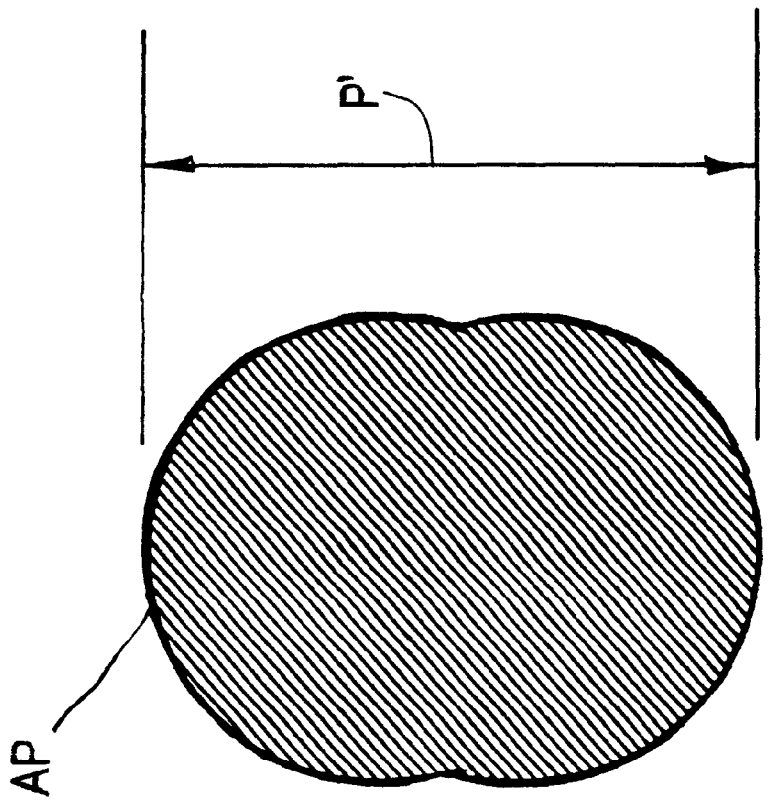
FIG. 11B illustrates a second increased dimension cross-sectional shape of the Type "B" fixation device in the second anchor configuration of FIG. 7 (taken along line 11B—11B of FIG. 7).
Figure 11A:
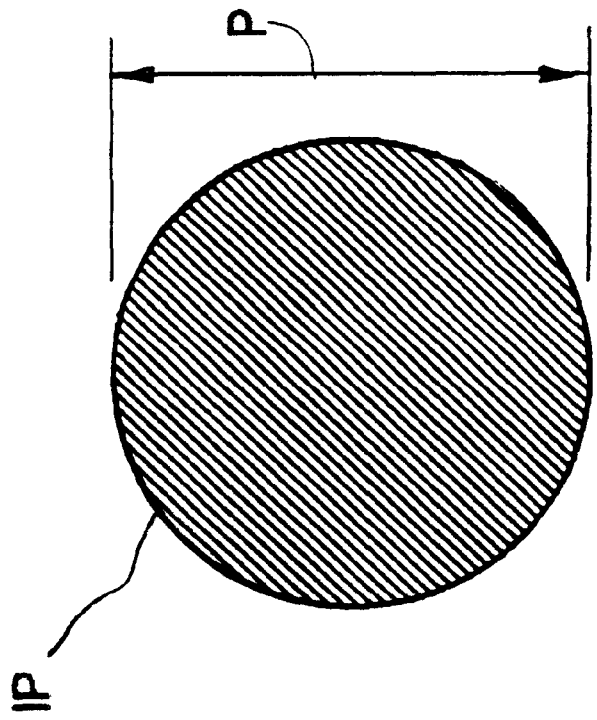
FIG. 11A illustrates a first cross-sectional shape of the Type "B" fixation device in the first insertion configuration of FIG. 6 (taken along line 11A—11A of FIG. 6).

As next shown in FIG. 10C, the physician alters the distal end of the polygonal driver 233 to the position indicated in FIG. 9B wherein the outer driver member 234a engages only polygonal bore portion 232a to thereby drive only first member 240A. The physician then rotates or drives first member 240A relative to the stationary second member 240B to alter body assembly 220 to the anchor configuration that provides an outer anchor periphery AP with an increased transverse dimension along the length of the body. Of equal importance, the relative helical movement of the paired first and second members 240A and 240B causes at least the distal portion of the member that is still driven to expose a sharp thread edge that engages the bone and graft. The continued driving forces on first member 240A causes the thread portion 229a of first member 240A to cut deeper into walls 111b around bore 101. At the same time, thread portions 229b of second member 240B engage the plug and press it radially outward Still further, the serrations 287 impressed in mating surfaces M and N of the first and second members 240A and 240B engage one another to lock the members in the counter-rotated or anchor configuration (see FIGS. 8A–8B). FIG. 11A illustrates the cross-section of body 220 (or insertion periphery IP) in the first position as when driving the body in FIGS. 10A & 10B. FIG. 11B then illustrates the cross-section of body 220 (or anchor periphery AP) in the second position after the first member 240 is advanced and rotated relative to the second member 240B.

Another embodiment of the Type "B" fixation body that is very similar to the device of FIGS. 6–7 can be adapted for rapid absorption of the fixation device in a patient's body, which may be desirable in certain procedures. This embodiment has first and second members 240A and 240B that have surfaces M and N without the gripping serrations 287 as depicted in FIGS. 8A–8B. In this alternative embodiment, the first member 240A is of a metal (or other sharp or durable material such as ceramic, plastic or combination thereof) and the second member 240B is of a bioabsorbable material. The paired members then can be driven into a bore or space as described above in both the Type "A" and "B" embodiments. The metal member is adapted to have a distal thread portion that is exposed and substantially sharp and durable in either a first or second helical position relative to the other cooperating member 240B. After the fixation body is driven to a desired depth, the first metal body member 240A, in situ, then can be rotated in a reverse direction to be de-mated from the other member and removed from the patient's body. This method then would leave only the bioabsorbable second member 240B in the bone. In this embodiment, the second member 240B may have its exterior that engages the bone configured with a serrated surface or toothed gripping surface to grip the bone to help insure that it will not rotate back out of the bone as the first member 240A is removed By using this technique, the helical space in the fixation body that is provided by removal of the first member allows faster tissue ingrowth into this space and around the remaining second body member—thus allowing for more rapid absorption of the second bioabsorbable member 240B. In this embodiment, the axes 225 and 245 may be offset or not offset with the key requirement being that the metal component provides the distal thread portion that is sufficiently sharp or durable to cut a path into the bone to accommodate the helical advancement of the remainder of the fixation body.

It should be appreciated that an alternative embodiment of a Type "B" offset helix screw (not shown) can be provided with has a central bore extending therethrough in the first position of FIG. 6. Thus, the driver 233 and the fixation body 220 may slide over a guide rod that is utilized to align the graft and the screw 220. The guide rod thus will maintain the first and second elements, 240A and 240B, in the first insertion position and can guide the screw into the bore in the desired location as is known in the art.

It also should be appreciated that another embodiment of offset helix screw may be provided in which a spiral thread axis is not offset from the axis of the helical mating interface. Rather, the spiral lead of the thread may be constant while the lead of the mating interface may have dissimilar or diminishing spiral lead dimension. In such a case, the axial and helical travel of one member relative to the another can be adapted to cause resilient second member to flex radially outward (relative to the first member) to a suspense configuration from a repose configuration, thus providing an offset helix screw having an insertion (repose) configuration with a lesser transverse dimension and an anchor (suspense) configuration with a greater transverse dimension (not shown).

It also should be appreciated that an offset helix fixation screw may be provided with a faster spiral lead thread for rapid driving into a bore in a bone, and a slower spiral lead associated with the mating interface to allow the surgeon more leverage at the moment he moves one member relative to the other member to the anchor configuration, thus reducing required driving torque during the insertion phase as well as reducing torque (by the principle of leverage) during the anchoring phase, when compared with conventional interference or anchor-type screws.

It also should be appreciated that an offset helix fixation device is not limited to surgical applications for anchoring a material in a bore, (e.g., attachments in bores in wood, plastic, concrete, gypsum board, etc.)

Those skilled in the art will appreciate that the exemplary embodiments and descriptions thereof are merely illustrative of the invention as a whole. Specific features of the invention may be shown in some figures and not in others, and this is for convenience only and any feature may be combined with another in accordance with the invention. While the principles of the invention have been made clear in the exemplary embodiments, it will be obvious to those skilled in the art that modifications of the structure, arrangement, proportions, elements, and materials may be utilized in the practice of the invention, and otherwise, which are particularly adapted to specific environments and operative requirements without departing from the principles of the invention. The appended claims are intended to cover and embrace any and all such modifications, with the limits only being the true purview, spirit and scope of the invention.

What is claimed is:

1. A fixation device comprising:
   an elongate body extending about a first axis of said body;
   the body comprising a first member and a second member that mate along a helical interface that extends about a second axis;
   wherein said helical interface provides for helical movement of said first member relative to said second member about said second axis between a first position and a second position;
   wherein said first axis is offset from said second axis; and
   wherein said offset axes thereby cause at least a portion of an outer periphery of said body assembly to be altered from a lesser cross-sectional dimension to a greater cross-sectional dimension when said first and second members are moved from said first position to said second position.

2. The fixation device of claim 1 wherein said body in said first position defines an outer periphery having a particular cross-section and in said second position defines an outer periphery having a greater cross-section in the distal end of the body.

3. The fixation device of claim 1 wherein said body in said first position defines an outer periphery having a particular cross-section and in said second position defines an outer periphery having a greater cross-section extending substantially along the length of the body.

4. The fixation device of claim 1 wherein said body in said first position defines a substantially cylindrical outer periphery for insertion into a bore and in said second position defines a conical outer periphery for anchoring said body assembly in the bore.

5. The fixation device of claim 1 further comprising a helical thread carried about the exterior of said body.

6. The fixation device of claim 1 wherein said second axis is angularly offset from said first axis.

7. The fixation device of claim 1 wherein said second axis is laterally offset relative to said first axis.

8. The fixation device of claim 1 wherein said first and second members are of a biocompatible metal.

9. The fixation device of claim 1 wherein at least one of said first and second members is of bioabsorbable material.

10. The fixation device of claim 1 further comprising a driver-engaging structure within the proximal end of said body.

11. The fixation device of claim 1 wherein said first and second members have cooperating faces along a helical mating interface, further comprising serrations in said faces for engaging one another.

12. The fixation device of claim 1 further comprising a longitudinal passageway extending between proximal and distal ends thereof.

13. The fixation device of claim 1 further comprising a suture or a loop attached to said fixation device.

14. The fixation device of claim 1 further comprising a gripping tooth surface in an exterior of the either the first or second member.

15. The fixation device of claim 5 wherein the radially-outward exposure of said helical interface between the first and second members is along the lands of said helical thread.

16. A bone fixation device, comprising:
   a fixation body assembly extending about a longitudinal axis;
   the fixation body comprising paired first and second members that slidably mate along a helical interface in said body;
   at least one helical thread formed in an exterior of the body assembly; and
   wherein in a particular relative helical position of the paired first and second members, a sharp distal portion of the helical thread of the first member is exposed for cutting into a bone.

17. The bone fixation device of claim 16, wherein the sharp distal portion of said first member is of a substantially strong material selected from the class consisting of metals, ceramics, plastics, or a combination thereof, and the second member is of a bioabsorbable material.

18. The bone fixation device of claim 16, wherein the second member is de-matable from the paired member in situ.

19. The bone fixation device of claim 16, wherein the second member is of resilient material.

20. A method for securing a fixation body in bone with a body assembly comprising first and second members that moveably mate about a helical interface of the fixation body to provide first and second relative helical positions of the first and second members, the central axis of the fixation body and the axis of the helical interface being offset, comprising the steps of:
   providing a bore in the bone;
   introducing the fixation body into the bore with the first and second members in the first position;
   moving the first member of the fixation body relative to the second member about the helical interface toward the second position;
   wherein the first position provides the fixation body with a lesser cross-sectional dimension to allow introduction into the bore with reduced force and the second position provides the fixation body with at least a portion having a greater cross-sectional dimension for anchoring the fixation body in the bore.

21. The method of claim 20 wherein the fixation body has at least one helical thread and the introducing step comprises helically driving the body into the bore.

22. The method of claim 20 wherein the moving step comprises applying a proximal tensioning force on either the first or second member to move the fixation body toward the second position.

23. The method of claim 20 wherein the moving step comprises applying torque to either the first or second member to cause relative helical movement between the members.

24. A method for securing an implantable body in a bone with a fixation body comprising first and second members that slidably mate along a helical interface in said body, said body having at least one helical thread formed in an exterior of the body, comprising the steps of:

helically driving the implantable body into the bone with the first and second members in a particular relative helical position that exposes a substantially sharp distal thread portion of the first member to thereby cut a path in the bone;

helically removing the first member of the body from the bone thereby leaving the second member in the bone; and wherein the free space provided by removal of the first member provides for more rapid ingrowth around the second member to secure the implantable body in the bone.

25. The method of claim 24 wherein the second member is of a bioabsorbable material.

* * * * *